(12) United States Patent
Russo

(10) Patent No.: US 9,656,022 B1
(45) Date of Patent: May 23, 2017

(54) ENTERAL MEDICATION DILUTING SYRINGE INFUSER

(71) Applicant: Ronald D. Russo, Naples, FL (US)

(72) Inventor: Ronald D. Russo, Naples, FL (US)

( * ) Notice: Subject to any disclaimer, the term of this patent is extended or adjusted under 35 U.S.C. 154(b) by 0 days.

(21) Appl. No.: 14/545,320

(22) Filed: Apr. 22, 2015

(51) Int. Cl.
 *A61M 5/24* (2006.01)
 *A61M 5/28* (2006.01)
 *A61M 5/315* (2006.01)
 *A61J 15/00* (2006.01)

(52) U.S. Cl.
 CPC ........ *A61M 5/2448* (2013.01); *A61J 15/0026* (2013.01); *A61M 5/284* (2013.01); *A61M 5/31576* (2013.01)

(58) Field of Classification Search
 CPC .......... A61M 5/2448; A61M 2005/202; A61M 2005/206; A61M 5/19; A61M 5/2033; A61M 5/31596; A61J 15/0026
 USPC ...................................................... 604/82–92
 See application file for complete search history.

(56) References Cited

U.S. PATENT DOCUMENTS

| | | | | |
|---|---|---|---|---|
| 4,116,240 A | * | 9/1978 | Guiney | A61M 5/31596 604/191 |
| 4,568,331 A | * | 2/1986 | Fischer | A61J 7/0007 206/221 |
| 5,464,393 A | | 11/1995 | Klearman et al. | |
| 5,472,421 A | | 12/1995 | Klearman et al. | |
| 7,347,394 B2 | | 3/2008 | Buckley | |
| 7,413,137 B2 | | 8/2008 | Donovan | |
| 7,427,041 B2 | | 9/2008 | Hall et al. | |
| 7,472,856 B2 | | 1/2009 | Sheavs | |
| 7,543,770 B2 | | 6/2009 | Peron et al. | |
| 7,648,093 B2 | | 1/2010 | Kruer | |
| 7,699,251 B2 | | 4/2010 | Frick | |
| 7,735,763 B2 | | 6/2010 | Bell et al. | |
| 7,896,273 B2 | | 3/2011 | Grah | |
| 8,033,488 B2 | | 10/2011 | Grah | |
| 2012/0289936 A1 | * | 11/2012 | Ingram | A61J 15/00 604/514 |
| 2012/0323173 A1 | * | 12/2012 | Thorne, Jr. | A61M 5/31596 604/89 |
| 2014/0207098 A1 | * | 7/2014 | Ingram | A61M 5/1452 604/500 |
| 2016/0058662 A1 | * | 3/2016 | Wheeler | A61J 1/10 206/571 |

* cited by examiner

*Primary Examiner* — Imani Hayman
(74) *Attorney, Agent, or Firm* — Robert J Doherty

(57) ABSTRACT

A combination medication diluting and infuser device in the form of an enteral irrigation syringe having an open-mouthed barrel portion with a piston positioned in the barrel wherein the open mouth of the barrel portion is provided with a replaceable sealing cap and wherein the barrel portion provides a medication-diluting chamber when medication and diluting fluid is introduced into the chamber via the open mouth thereof and can be mixed in the diluting chamber prior to infusing the diluted medication into the patient via a top opening provided in the sealing cap.

4 Claims, 9 Drawing Sheets

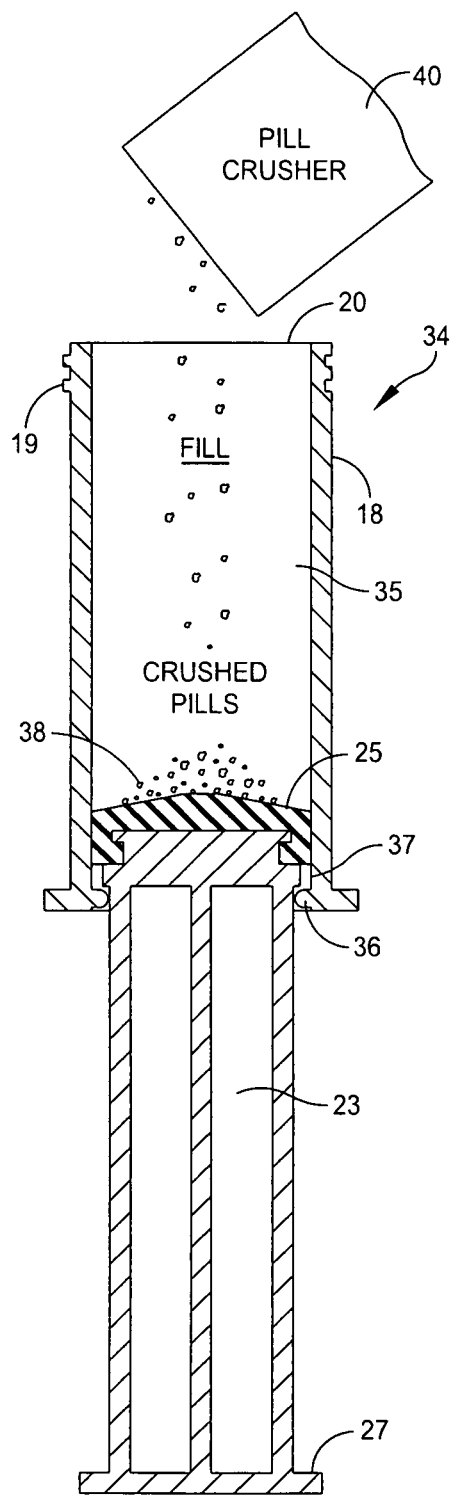
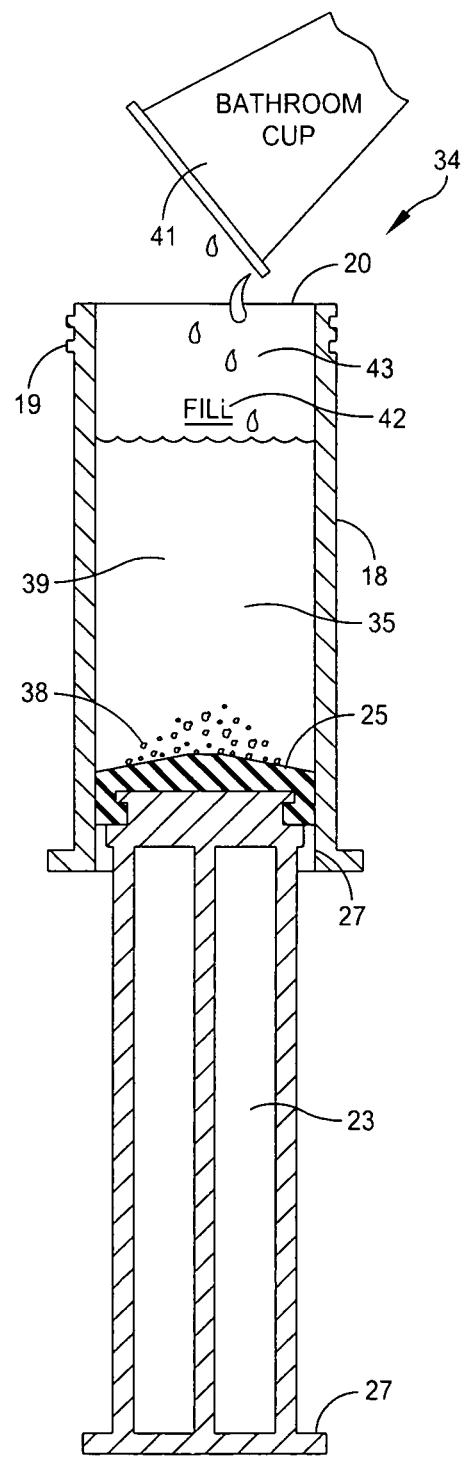
FIG. 4                    FIG. 5

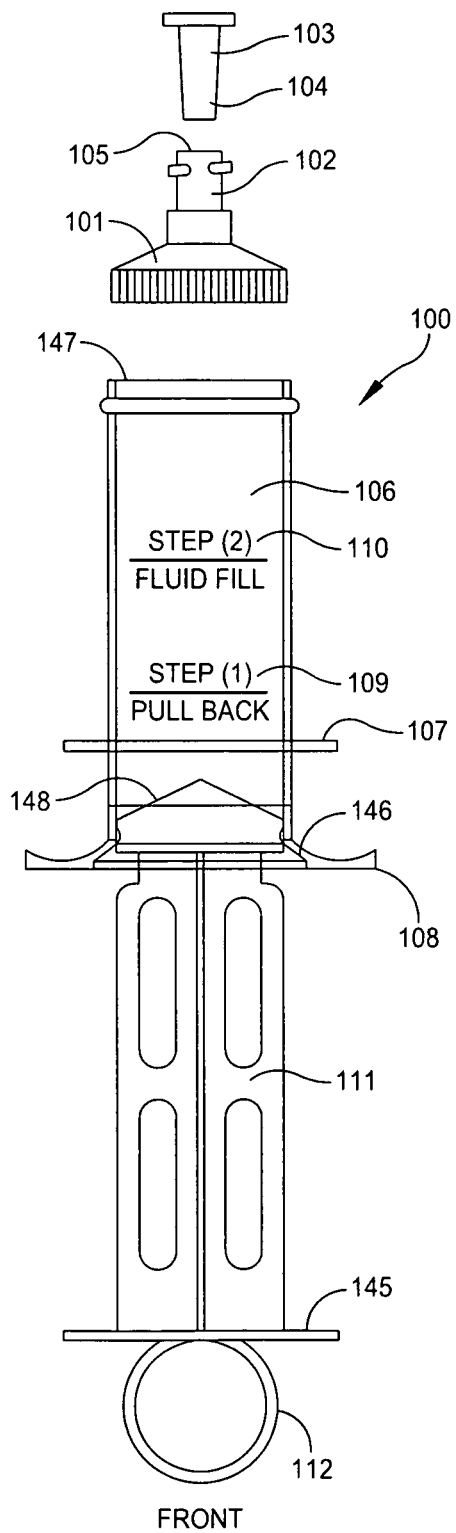
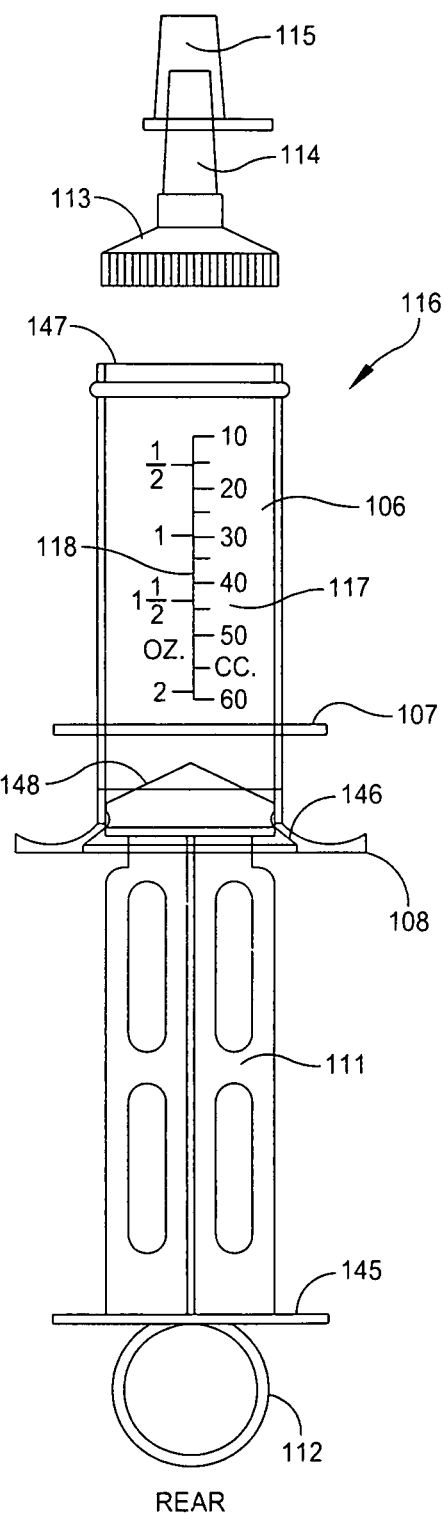
FIG. 11
FIG. 12

ENTERAL MEDICATION DILUTING SYRINGE INFUSER

Applicant claims the benefit of U.S. Provisional Patent Application No. 61/995,926 filed Apr. 25, 2014.

BACKGROUND OF THE INVENTION

Feeding tubes are routinely placed in patients who lose their ability to feed themselves. Such tubes fall into two categories of naso-enteric tubes, gastrostomy or gastro jejunal tubes. Small-bore naso-enteric tubes are Salem sump or Levin tubes ranging from 12 fr up to 20 fr in size, whereas gastrostomy and gastro jejunal tubes typically have larger bores ranging from 18 fr up to 28 fr.

Small-bore enteral feeding tubes may become clogged in up to 35% of patients. Various factors contribute to tube occlusions including high viscosity enteral formula, feeding tube characteristics, insufficient flushing, and incorrect medication delivery—all reported in the medical literature.

Enteral liquid nutrition is delivered by gravity, pump, or bolus syringe feeding using formula such as Ensure®, which is a soy-based formula.

These tubes must be routinely flushed or irrigated before and after delivery of the liquid formula to prevent tube clogging. Such patients also routinely require the administration of medications through the tube because of their inability to swallow.

Typically, pills or tablets are crushed. The crushed pills or tablets are then manually dissolved in a small vessel such as a cup by adding water and physically stirring the contents and then aspirated, that is, drawn up, into a separate catheter-tip or enteric-tip administering syringe, and then ultimately the syringe used to infuse the medication into the feeding tube.

Manually stirring the crushed pills or tablets in a bathroom cup or specimen container often leaves behind undissolved bits and pieces of the crushed medication in the administering syringe that often clogs the feeding tube. Once clogged, the tube often cannot be unclogged requiring the removal and replacement of the tube that is traumatic to the patient and a costly unnecessary repeat medical procedure.

Liquid medications are sometimes available, but the sorbitol preservative in the liquid medications often negatively react with the enteric liquid soy-based Ensure® formula by congealing with the formula and solidifying within the tube to gum up or otherwise clog the tube with congealed formula. As such, liquid medication requires dilution with water to permit non-clogging administration.

Crushing and manually stirring and dissolving pills or tablets are a routine method of preparing medications for syringe infusion into a feeding tube because the pills do not contain the sorbitol preservative.

A variety of pill or tablet crushers are readily available in the marketplace. The classical use of the mortar and pestle to crush medications is also commonplace. However, just stirring the crushed pills or tablets does not sufficiently dissolve pills or tablets such that infusion of the medication leaves bits and pieces lodged within the tube to clog the tube.

While the prior art is replete with many pill crushers, there is no available known device which will effectively and completely dissolve the pills or tablets after they are crushed to prevent tube clogging during syringe infusion.

It would be extremely useful and beneficial to provide a device that would effectively and completely dilute and dissolve all forms of medication whether individual pills, crushed pills, liquid medication, or powder medication and which would also act as a convenient combination device for infusing the medication into a feeding tube after the medication is dissolved.

Toward this end, the present invention has been conceived.

Other objects, features and advantages of the invention shall become apparent as the description thereof proceeds when considered in connection with the accompanying illustrative drawings.

SUMMARY OF THE INVENTION

A combination enteral medication diluting and syringe infuser device is herein disclosed.

The device is a self-contained, single-patient use, ready-to-use, disposable product that effectively and completely dissolves the crushed pills or tablets and simultaneously acts as an enteral syringe infuser to administer the thus dissolved crushed pills or tablets without the need for a separate syringe. The device of the subject invention also acts to dilute and administer all other types of medication whether individual tablets, liquid medication or powder medication into all types of enteral feeding tubes.

Preferably, the device takes the form of five injection-molded components comprising:

a screw cap with a tube infusion tip, a closure for sealing off the tip, a wide open-mouthed syringe barrel, a slidable piston positioned within the barrel providing an aspiration and infusion syringe action within the barrel, and a sealing grommet or "O" ring formed on top of the piston to provide a slidable sealing action for the piston while the piston is sliding within the barrel.

The device accepts all types of pills or tablets once crushed by any crushing means or device as well as all other types of medication, and the wide-mouth opening easily accepts the receipt of the diluting fluid (generally water).

In addition, the device can be used to flush enteral feeding tubes with water before and after drug delivery and to dilute liquid medications particularly those liquid medications that are highly concentrated or viscous. Such dilution helps reduce the medication viscosity that increases fluid flow through small-bore feeding tubes to prevent tube occlusion and increase drug delivery rates.

The device is compact, easy to use and inexpensive. The device can be rinsed and re-used for generally up to 24 hours of use or can be discarded after each use, if desired. The device of the instant invention can also function just like any other catheter tip irrigation syringe for flushing or irrigating the feeding tube during the 24-hour period to eliminate the need for a separate irrigating syringe thereby offering convenience and hospital cost savings.

DESCRIPTION OF THE DRAWINGS

In the drawings which illustrate the best mode presently contemplated for carrying out the present invention:

FIG. 4 is a front view of the device depicting the piston portion fully retracted and crushed pills being poured into the wide-mouth opening of the barrel;

FIG. 5 is a front view of the device from FIG. 4 wherein warm diluting water is being poured into the wide-mouth opening of the barrel;

FIG. 11 is a front ready-to-be assembled view of a commercial first alternate embodiment of the device depicted in FIG. 8 having the proposed ISO/ANSI 80369-3 female screw thread tip with imprinted diluting instructions stamped or otherwise printed on the front of the syringe barrel;

FIG. 12 is a front ready-to-be assembled view of the commercial embodiment of the device depicted in FIG. 11 having a traditional catheter tip with either molded or imprinted volume graduations provided on the rear of the syringe barrel;

DETAILED DESCRIPTION OF THE INVENTION

The prior art is filled with various pill crushing devices such as U.S. Pat. No. 7,735,763 issued January 2010 to Bell et al. and U.S. Pat. No. 8,033,488 issued October 2011 to Grah. Both of these recently issued patents also list the relevant prior art patents as references. Nurse Assist, Inc.'s Welcon® brand commercial pill crusher product No. 3305 should also be noted as a prior art device along with several other commercial pill crushers from Apothecary Products Corp. in Minneapolis, Minn. The patents to Klearman et al., namely U.S. Pat. No. 5,464,393 issued Nov. 7, 1995 and U.S. Pat. No. 5,472,421 issued Dec. 5, 1995, should also be noted.

While these devices may effectively crush pills or tablets, these devices do not offer a convenient and effective combination means for first dissolving the pill/tablet and then infusing the dissolved medication into the patient through the patient's feeding tube.

As such, the present invention represents a substantial advancement in the state of the art by disclosing a combination medication diluting and infusing device for use in administering all types of medication into a patient's feeding tube.

Figure 1:
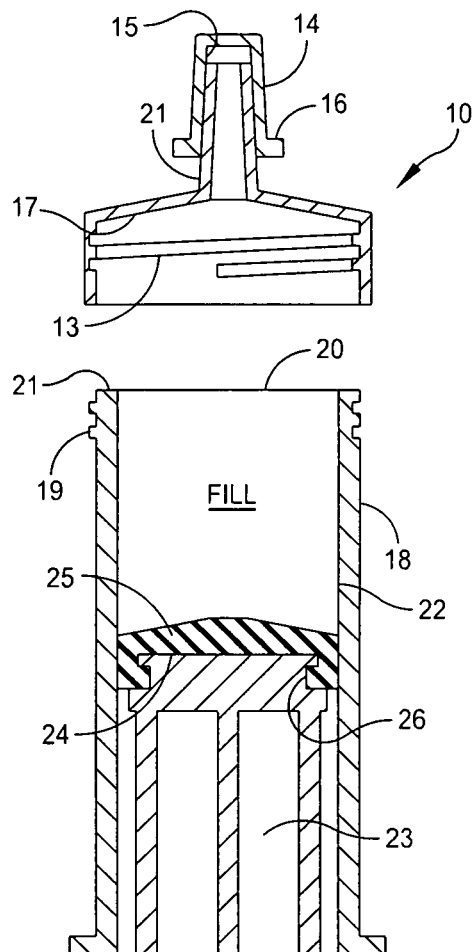
FIG. 1 is a front partially assembled view of the device of the present invention.

Turning to the drawings, FIG. 1 depicts a front view of a partially assembled medication diluter and infuser syringe device 10 comprising a polypropylene plastic injection molded cap 11 having a built-in nozzle tip 12. The tip 12 can take the form of a traditional catheter tip or the smaller enteric syringe tip configuration. The cap 11 has internal threads 13. The tip 12 may be closed off by a flexible injection molded closure 14 that can be formed from flexible PVC or synthetic rubber such as Kraton or even dip molded.

The closure 14 has a tapered internal wall 15 that acts to positively form a leak-proof seal with the tip 12. The closure 14 can serve to either close off the tip 12, or when the tip 12 is removed, the closure 14 can open up or expand the nozzle tip 12. A lower flange 16 or extension tab can be molded into the closure 14, which aids in manually attaching or removing the closure 14 from the tip 12. The cap 11 incorporates an internally molded-in smooth inner sealing surface 17. In addition, the tip 12 can take the form of or assume any configuration such as a nozzle, a reverse threaded luer or any type of non-luer tip compatible configuration to prevent accidental connection to a female I.V. luer catheter. While the closure 14 is depicted as a completely removable component, the closure 14 could easily be designed and configured to have an extended integrally tethered strap so as to have closure 14 remain an integral part of the nozzle tip 12 thus preventing loss or misplacement when removing or replacing the closure 14 from the nozzle tip 12.

The cap 11 is both removable and replaceable to form a sealing engagement with the syringe barrel 18 and is also preferably injection molded from a relatively clear polypropylene such that the contents within the barrel can be easily viewed. The barrel 18 has mating external screw threads 19 which engage with the internal threads 13 on the cap 11 to form a leak-proof sealing engagement with the top opening 20 on the barrel 18. The top opening 20 is wide-mouthed, that is, about 1.250 inches in diameter. Adjacent to the opening 20 is a sealing surface 21 that forms a mating leak-proof sealing engagement with the smooth inner sealing surface 17 on the cap 11 when the cap 11 is screwed onto the barrel 18 to close off the opening 20 on the barrel 18. The barrel 18 has internal straight-sided walls 22 having a wall thickness of about 0.070 inches. Positioned and inserted within the barrel 18 is a retractable and advanceable piston 23 that is also injection molded from polypropylene.

The piston 23 has a top surface 24 onto which is fitted a synthetic rubber molded grommet 25 that is snap fitted on the top surface 24 and held in place utilizing the undercut 26 on top surface 24 formed during the molding process. The grommet 25 provides a leak-proof slidable seal between the outer wall surfaces of the grommet 25 and the inner walls 22 on the barrel 18. A thin film application of medical grade silicone oil may be applied to the grommet 25 to aid in providing a smooth manual retracting or advancing action of the piston 23 within the barrel 18.

The piston 23 can also incorporate a lower grip flange 27, which aids in the manual travel action of the piston 23. The cap 11, barrel 18, and piston 23 are all configured in a circular diameter configuration typical of all catheter tip syringes. The piston 23 also has thin-molded walls of about 0.070 inches in thickness.

Figure 2:
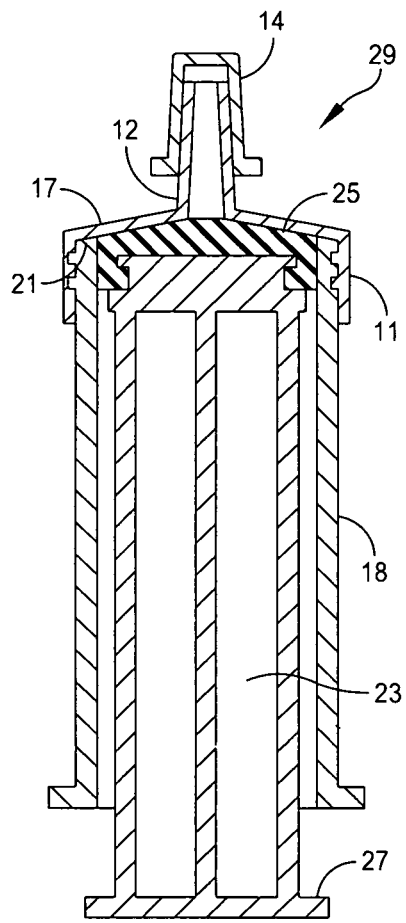
FIG. 2 is an assembled cross-sectional view of the device shown in FIG. 1.

FIG. 2 depicts the assembled medication diluting and infuser 29 shown in its partially assembled form from FIG.

1 as reference numeral 10. It should be noted that assembled medication diluting and infuser 29 is very compact and generally less than six inches in total length when fully assembled and is designed as a disposable, single patient use product.

Figure 3:
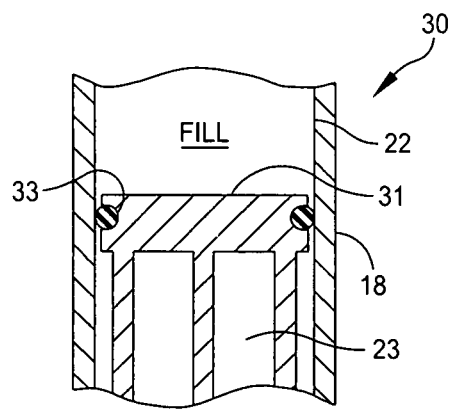
FIG. 3 is a partial view of the barrel and piston portion of the device wherein the piston has an "O" ring slidable wiper seal.

FIG. 3 depicts an alternate "O" ring design 30 compared to the grommet 25 design depicted in FIG. 1. The "O" ring design 30 utilizes the same barrel 18 with piston 23 only having a flat top 31 with molded-in "O" ring 33. A small drop of medical grade silicone oil applied to the "O" ring 33 also helps in providing smooth retracting and advancing action of the piston 23 within the barrel 18 of the alternate "O" ring design 30 shown in FIG. 3.

FIG. 4 is a front view of the device 34 wherein the cap 11 (not shown) as depicted in FIGS. 1 and 2 is removed from the opening 20 on the barrel 18 and wherein the piston 23 is fully retracted within the barrel 18 to form an inner pill and fluid diluting receptacle chamber 35. A piston retracting stop ring 36 can be molded or otherwise incorporated into the lower portion 37 of the barrel 18 that will function as a piston-retracting stop thus preventing the piston 23 from being completely removed from the barrel 18.

The top opening 20 on the barrel 18 is sufficiently wide mouthed, e.g., 1.250 inches, to permit the barrel 18 to accept both the crushed pills 38 and the diluting fluid 39 as shown in FIG. 5 and manually poured into inner diluting receptacle chamber 35 as illustrated by FIGS. 4 and 5.

It should be noted that any type of medication such as an individual tablet, liquid medication, or powder medication could also be manually poured into the chamber 35. These include medications such as Mylanta™, Kaopectate™, Immodium™, or powder laxatives.

The top opening 20 is large enough to manually accept one or more crushed pills 38 directly from any pill crusher cup 40 or device and dissolving fluid 39 can also be subsequently directly manually poured from any drinking or other paper cup 41 as shown in FIG. 5 into the inner receptacle diluting chamber 35.

The initial manual pouring of pre-crushed pills 38 through top barrel opening 20 permits 100% of the already pre-crushed pills 38 to be housed and retained within the diluting dissolving chamber 35.

Likewise and most importantly, the novel concept of next manually pouring in the diluting dissolving fluids 39 directly through the top opening 20 into the lower diluting receptacle chamber 35 means there is absolutely no loss of pre-crushed pills 38 or dissolved fluid 39 out of the nozzle tip 12 on cap 11 shown in FIGS. 1 and 2, because the nozzle tip 12 is not used as a means to aspirate dissolving fluid 39 into syringe barrel 18 as in the prior art.

After considerable research, it has been determined that the ideal volume of dissolver fluid 39 is 30 ml of warm water wherein a liquid fill indicator line 42 clearly indicates the 30 ml proper fill level into dissolving chamber 35. The indicator line 42 can easily be molded into barrel 18 or can be visibly ink printed along with milliliters and/or ounce graduations, if desired.

It should be noted that the total fluid volume of chamber 35 is 40 ml such that a residual top volume 43 of 10 ml is left as shakable air space. The total volume of chamber 35 however can easily be increased to 60 ml.

As can be seen from FIGS. 4 and 5, the piston 23 remains in its fully retracted position to create and form the inner diluting receptacle chamber 35. The sealing grommet 25 mounted on top of the piston 25 acts to seal off any leakage or loss of either crushed pills or fluid 39 out through the lower portion 37 of the barrel 18.

Figure 6:
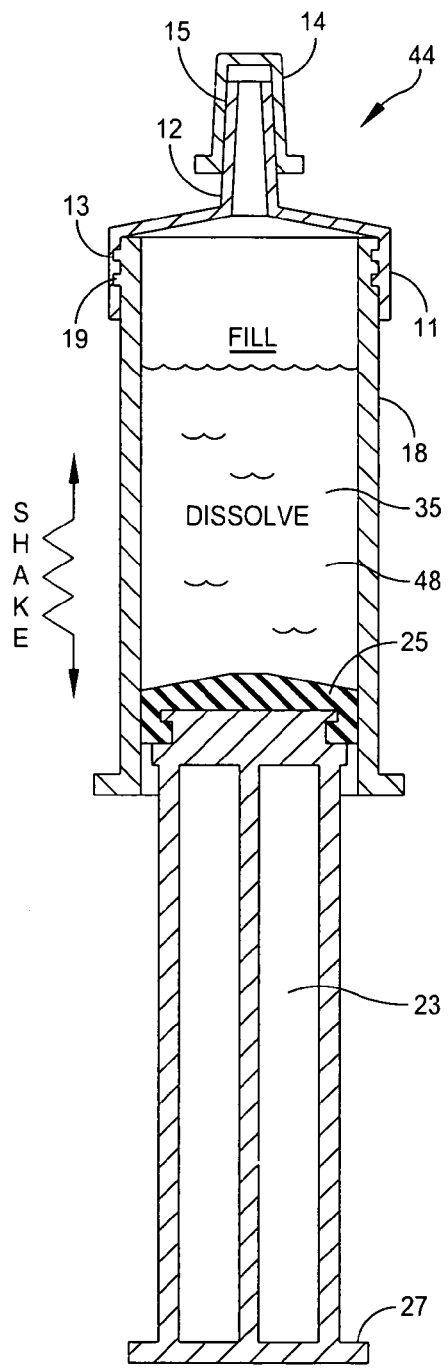
FIG. 6 is a front view of the device wherein the cap enclosure covers the wide-mouthed opening and the crushed and dissolved pills are shaken within the device.
Figure 7:
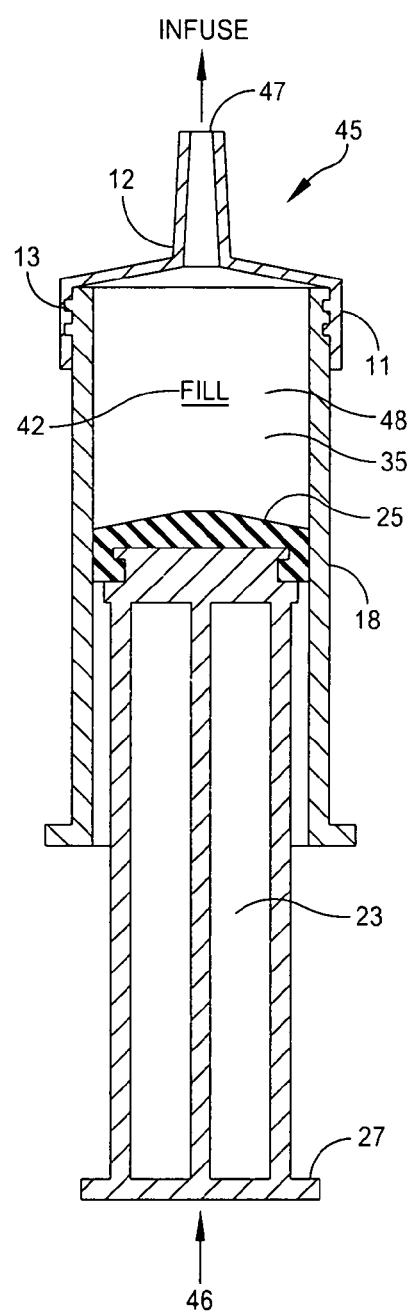
FIG. 7 is a front view of the device from FIG. 5 wherein the thoroughly crushed and dissolved pill is infused into a feeding tube.

Further research has determined that the most effective manner and procedure to effectively and completely dissolve bits and pieces of crushed pills 38 as shown in FIGS. 4 and 5 is to vigorously shake the device and thus the contents within the dissolving chamber 35 such that the crushed pills 38 become completely dispersed and dissolved into the medication delivery solution 48 as depicted in combination pill dissolver 44 from FIG. 6 and liquid syringe infuser 45 as shown in FIG. 7. The foregoing is accomplished when the cap 11 with the cap's attached closure 14, which closes off nozzle tip 12, is replaced and screwed back onto the barrel 18 to, in effect, seal off the inner chamber 35 as shown in FIG. 6 in a leak-proof manner.

The diluting device 44 now can convert the diluting receptacle 35 to further act as a shakable medication and fluid diluting dissolving chamber when the cap 11 is replaced and the nozzle tip 20 is sealed by the closure 14. Shaking time is usually about 30 seconds or so or until all crushed pills are visually dissolved when looking through the barrel 18 into the chamber 35. Of course, finger or thumb pressure could be used to close off the nozzle tip 12 while shaking the device 44 but would not be as convenient as using the closure 14.

It has been determined that shaking the device 44 for thirty seconds or so using warm water will result in a completely dissolved solution 48 as shown in FIG. 6 thus eliminating the undesirable bits and pieces of crushed pills or tablets that often clog enteral feeding tubes or diluted liquid or powdered medications, which are in a suspension fluid form. Merely stirring the crushed pills in a separate fluid container or cup (as in the prior art) will not effectively or completely dissolve these bits and pieces.

Experiments have further determined that as little as 10 ml of fluid is capable of dissolving a small pill within barrel 18, but the use of 30 ml to fill line 42 is recommended for the majority of pills, tablets, liquids or powders.

Once the pills 38 are completely diluted and dissolved after shaking, the device 45 as shown in FIG. 7 is now ready to be conveniently used as the syringe infuser as shown. In FIG. 7, the closure 14 is removed and nozzle tip 12 is opened such that the device 45 can be connected or attached to any enteral feeding connector, tube, or catheter whether naso-enteric or gastro-jejunal.

The device 45 can now be used as a versatile, universally applicable enteric syringe performing all the required usages of such a syringe such as tube flushing/irrigation, medication dilution, pill dissolving, medication infusion, and delivery of enteric syringe bolus formula feeding.

The piston 23 can now be advanced as shown by arrow 46 to infuse or instill the dissolved solution 48 out of nozzle tip 12 through lumen 47 on tip 12.

The unique construction, design, and method of using the device 44 and 45 as shown and described in FIGS. 6 and 7 demonstrates that the device is a self-contained, completely closed medication retention system ensuring that 100% of the diluted and dissolved medication is delivered to the patient and is retained within chamber 35 ready to be infused without fear of losing or spilling any medication while crushing, pouring, diluting, dissolving, shaking, and infusion of the medication delivery procedure as outlined above.

If any dissolved solution residue is visible through the clear polypropylene barrel 18, the device 45 can then be readily used as an irrigation syringe by merely using piston 23 to aspirate 30 ml of irrigation water from a cup or other receptacle back into the barrel 18 and then reconnecting the device 45 back onto the enteral connector or feeding tube for repeated irrigation.

The device may have a typical catheter tip configured nozzle tip 12 or the cap 11 can be configured to have an enteric tip configuration as utilized in the Covidien™ Monoject™ enteric purple or oral syringe product lines.

As clearly depicted in FIG. 7, the device can be rinsed thoroughly and re-used as often as desired during a full 24-hour period. However, the device 45 is so inexpensive that the device 45 can be used one time, disposed of after each use, and utilized as any other 60 ml enteral syringe. The device 45 may be packaged in an inexpensive polyethylene bag and is non-sterile, single patient use, and ready to use right out of the package.

Figure 8:
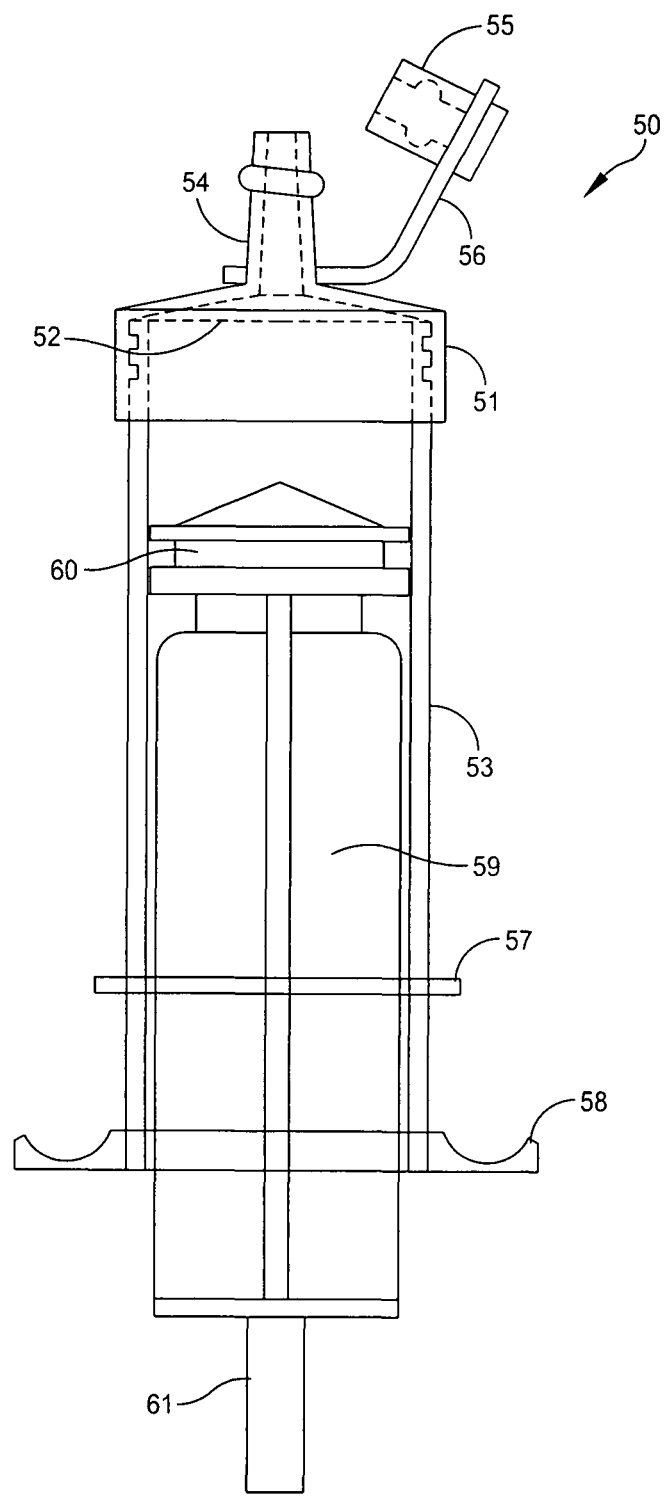
FIG. 8 is a front view of a first alternate embodiment of the device having a female threaded tip in conformance with proposed ISO/ANSI 80369-3 enteral tip standard, a tethered closure and a thumb ring single-handed operable syringe.

FIG. 8 depicts an alternate combination diluting and syringe infuser device 50 having a similar structure as depicted in FIGS. 1-7. However, the device 50 is shown having an injection molded polypropylene screw cap 51 that closes off the barrel opening 52 on the injection molded polypropylene barrel 53. The screw cap 51 differs from previous caps depicted in that this screw cap 51 has a molded-in, built-in female luer lock tip 54. The tip 54 is so dimensioned to conform to ISO/ANSI 1986 standards for luer tips.

Since the tip 54 is configured as a female luer, the tip 54 cannot mechanically mate to an identical rigid female luer connector used as part of any standard I.V. catheter. This non-mating incompatibility feature prevents the syringe 50 from connecting to any I.V. female luer connector I.V. catheter, which is a safety feature to prevent enteral formula delivery into an I.V. catheter. As such, the female luer syringe tip 54 can only mate with a male connector that is used in some European manufacturers feeding tubes such as Medicina's line of naso-enteric tubes.

In addition, the tip 54 can be sealed or otherwise closed off with the separate male closure 55 which incorporates a tethered built-in strap 56 to prevent losing the closure 55 during use. Further, while the tip 54 is shown as a molded-in female luer, the cap 51 can have any other type of molded configuration such as an enteric, oral or medication delivery tip.

The tip can easily be configured to conform with any proposed ISO/ANSI enteral connector design standard 80369-3, for example, wherein the tip 54 is a female enteral screw thread design having a nominal internal diameter of approximately 5.26 mm, which is far in excess of a standard male luer tip having an internal diameter of only between 1.75 mm to 2.4 mm. Such a female threaded tip would absolutely prevent misconnection with female luers on I.V. catheters.

Also, finger rings 57 and 58 can be molded into the barrel 53 that assist in single one-handed operation of the device 50 in conjunction with the piston 59 having a grommet 60 and built-in piston thumb ring 61.

Figure 9:
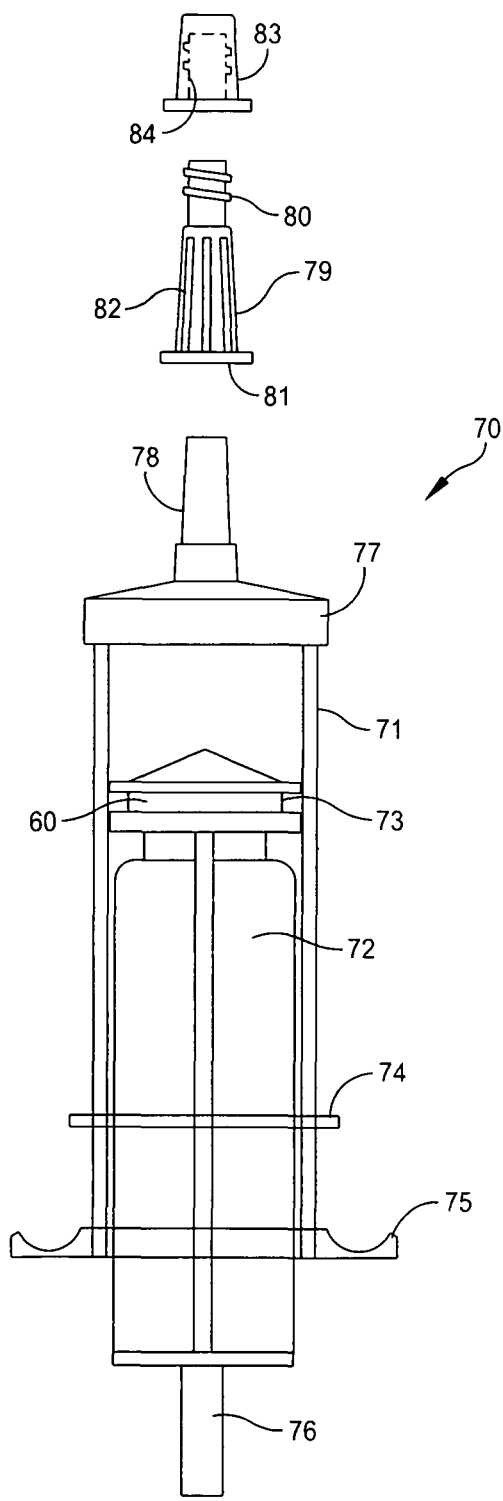
FIG. 9 is a front view of a second alternate embodiment of the device having a traditional catheter tip cap with a separate adapter and closure which converts the device over to the proposed ISO/ANSI 80369-3 female screw-threaded tip.

FIG. 9 depicts a second alternate embodiment syringe 70 having barrel 71, piston 72, and grommet 73 wherein barrel 71 has integral finger grips 74 and 75 and a thumb ring 76 molded into the piston 72.

It should be noted that when the barrel 71 is elongated to a full 60 cc capacity, the syringe 70 is fully capable of being used as a full utility enteral formula or irrigation syringe. The screw cap 77 includes an integral catheter tip nozzle 78 as previously described above in connection with the FIG. 1 description. However, it should be noted that the female screw threaded adapter 79 having an external screw threaded tip 80 to conform with recently proposed ISO/ANSI 80369-3 tip standards can be used to convert the catheter tip 78 over to the non-luer compatible tip 80.

The adapter 79 can be injection molded in one piece having a mating internal taper 81, which forms a press-fit with tip 78. Grip lines or ridges 82 may be molded into the adapter that can assist in the above-described press fit action. The screw cap closure 83 having mating internal screw threads 84 can engage with the external screw threaded tip 80 to both seal off and open up the tip 80 as needed during the shaking, dissolving and fluid administering procedure.

Just as easily, the cap 77 can be alternatively molded to incorporate built in proposed ISO/ANSI 80369-3 external screw thread tip 80 instead of the catheter nozzle tip 78 shown in FIG. 9. In this reverse configuration, adapter 79 would have a catheter nozzle tip configuration which would screw into the mating ISO/ANSI tip on the cap 77. In that configuration, the nozzle tip 78 would utilize a closure such as the flexible Kraton molded closure 14 shown in FIG. 1.

Either way, the cap 77 can have a removable adapter 79 configured to provide either a catheter tip nozzle 78 or proposed ISO/ANSI 80369-3 external screw threaded tip 80, such that the cap 77 has a fixedly molded-in tip configured to accept a removable enteral connector adapter.

In this second embodiment, the syringe 70 can now be used as a traditional catheter tip 78 or easily adapted for use in the proposed ISO/ANSI 80369-3 tip 80 using the adapter 79. The adapter 79 can easily be packaged as part of a syringe kit to offer maximum device versatility along with the closure 83.

Figure 10:
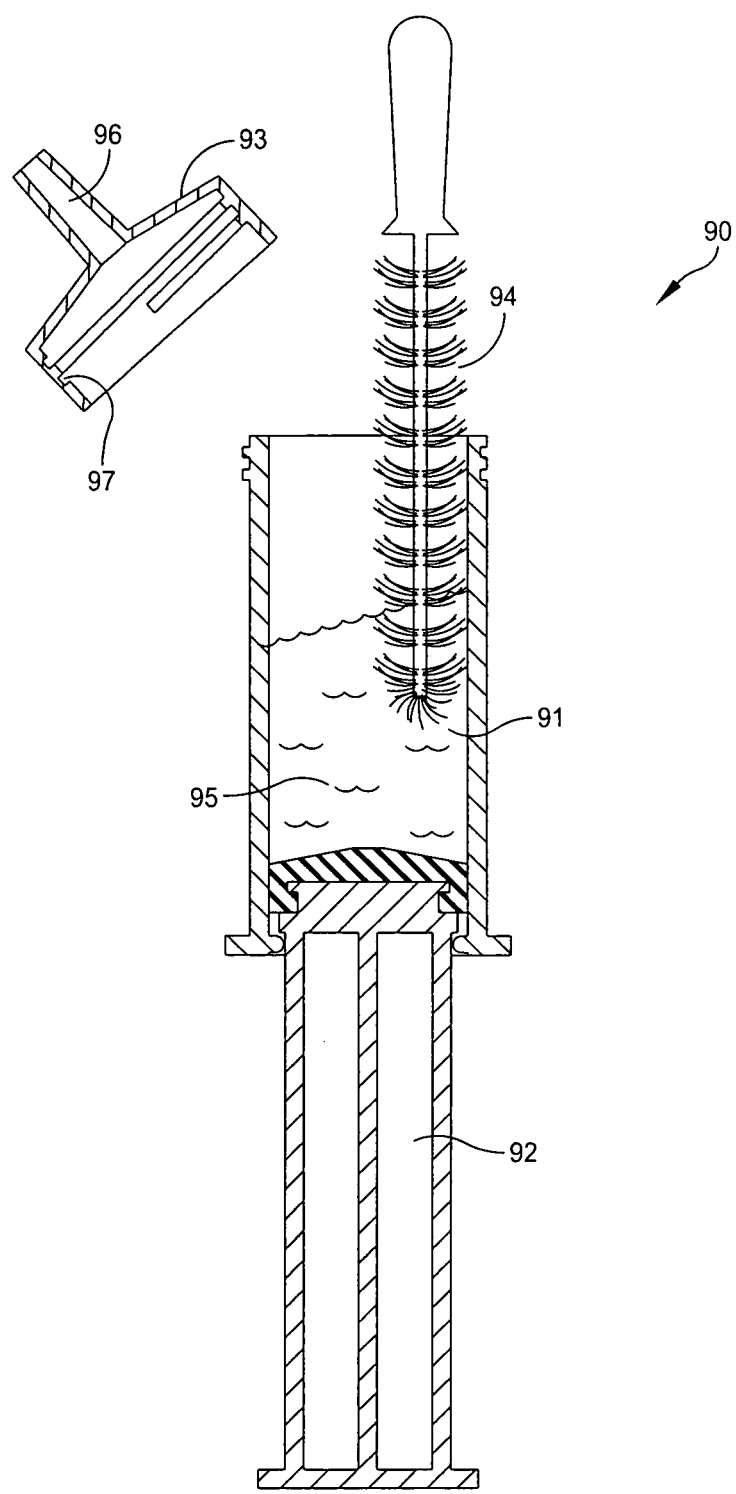
FIG. 10 is a front view of the device shown in FIGS. 1-7 with its cap removed and piston retracted depicting the ease of internally brush cleaning both the barrel and cap after administering medication or bolus enteral formula.

FIG. 10 depicts a device 90 having a barrel portion 91 with the piston 92 retracted and the cap 93 removed. The removable cap 93 allows for thorough internal cleaning of both the barrel 91 and the cap 93 using a readily available baby bottle nipple cleaning brush 94 from manufacturers such as Kiinde Inc. or Munchkin Inc. These cleaning brushes are very inexpensive at around $6.00 for a package of two brushes and can be used repeatedly especially for home care patients and are dishwasher safe as well. Any readily available toothbrush could also be used.

The top opening access feature of the device 90 permits the use of liquid dishwashing soap and water 95 along with the brush 94 to thoroughly clean any residual formula film left within the barrel 91 or cap 93 after administering soy-based enteral formula such as Ensure®.

In addition, the internal threads 97 and the nozzle tip 96 portion of the cap 93 can also be cleaned using the same liquid soap and water 95. After thorough cleaning and rinsing both the barrel 91 and retracted piston 92 along with the cap 93, the device 90 can be left to air dry on a standard kitchen dish drying rack ready for its next use. As previously noted, it is generally recommended that the device 90 be for a single patient's use and should be discarded after 24 hours of use, both in the hospital as well as in a home care setting.

This type of thorough internal surface cleaning of the device 90 is not easily achieved with traditional syringes which require the piston to be removed to gain access to the inside of the syringe.

It is virtually impossible to access and thoroughly clean the internal passageways of any traditional catheter tip syringe. The fact that you can clean the internal passageways as shown in FIG. 10 with or without a brush is a very important feature to prevent the proliferation of bacteria such as C-diff leading to GI problems especially in immunocompromised patients. Unlike traditional syringes, once the cap 93 and nozzle tip 96 are removed from the barrel 91, the cap 93 and nozzle tip 96 can be easily cleaned using a common dishcloth or by dipping and/or agitating in a basin of warm soapy water along with a final rinse of fresh water.

The use of brush 94 to clean both the barrel and the cap with nozzle is a nice feature. However, brush cleaning is not a mandatory requirement because, unlike traditional syringes, the barrel, cap and nozzle can be easily cleaned with or without a brush. If cleaned without a brush, a simple dishcloth or rinsing in water will suffice.

As such, the unique top loading and internal access feature of the device 90 is essential to reduce bacterial growth within the syringe. FIG. 11 is a ready-to-be assembled front view of the medication and infuser syringe 100 having a cap 101 with a proposed ISO/ANSI 80369-3 female screw thread tip 102 integrally molded in as part of the cap 101, which are plastic injection molded from natural polypropylene as previously shown and described in FIG. 8.

The closure 103 is also injection molded from polyethylene and has a tapered plug portion 104 that acts to seal off the interior flow passage 105 on the cap tip 102. The barrel portion 106 is also injection molded from natural polypropylene and has built-in or integral finger grips 107 and 108. Graphically pad printed on the barrel 106 are easy-to-read medication diluting instructions 109 and 110 instructing the user in Step 1 to first retract the plunger 111 to the pull back line and secondly diluting the pour in medication up to the Step 2 fluid fill line. The thumb ring 112 coupled with the finger grips 107 and 108 aids in one-handed operation of the syringe 100.

From FIG. 11, the barrel portion 106 includes a step one visual piston retraction indicator marking 109 along with step two subsequent visual diluting fluid level indicator marking 110. Both visual markings 109 and 110 aid in permitting the proper manual pouring acceptance of both medication and diluting fluid into the barrel portion 106 through the top opening 147.

FIG. 12 depicts a similar syringe 116 but incorporating a traditional screw cap 113 with a catheter tip 114 and closure 115, which are all shown and described above relative to the FIG. 2 description. The barrel portion 106 and piston 111 are exactly the same components as shown in FIG. 11 except FIG. 12 now depicts the rear view 117 on the barrel 106 having volume graduations 118 wherein the same medication and diluting syringes 100 or 116 can also be used to administer flushing irrigation or bolus formula delivery up to 60 cc.

From FIGS. 11 and 12, there is also shown and described lower circular piston flange 145 on piston 111, which is dimensionally oversized to about 1.400 inches in diameter that acts as a piston advancement travel limiter stop against dimensionally undersized lower circular internal barrel diameter surface 146 having a slightly undersized diameter dimension of 1.300 inches which forms an undersized interference abutment.

This dimensionally oversized circular piston flange 145 engaging the undersized interference abutment configuration acts as a convenient molded-in means for preventing resilient, smooth-surfaced Kraton or silicone molded grommet 148 on piston 111 from exiting out the top barrel opening 147 when the cap 101 from FIG. 11 or cap 113 from FIG. 12 is removed or disengaged from the barrel 106 shown in FIGS. 11 and 12.

Figure 13:
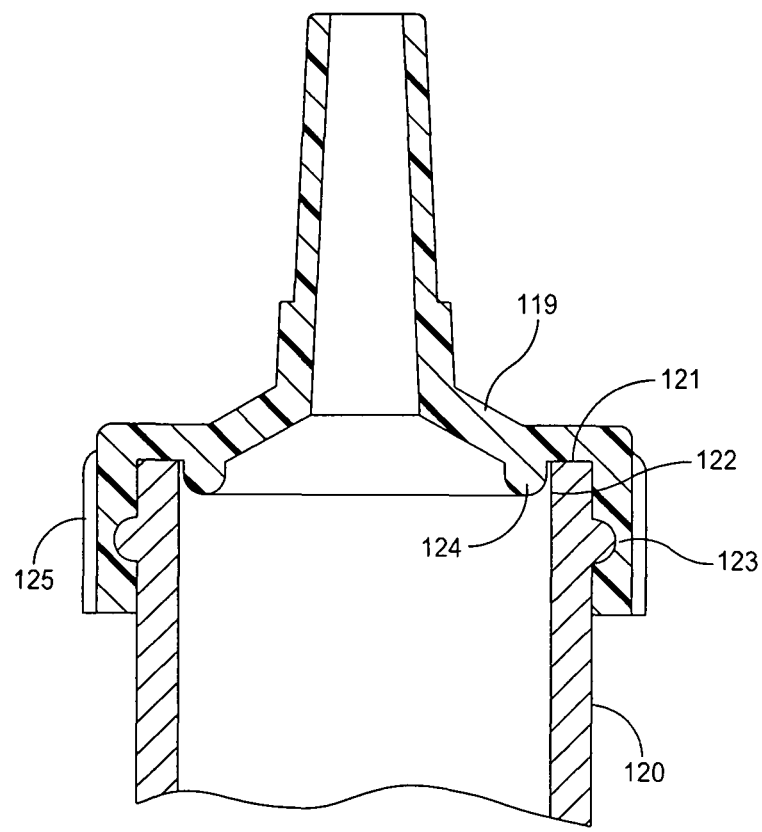
FIG. 13 is an enlarged partial cross-sectional view of the cap to barrel threaded sealing engagement construction of the device depicted in FIG. 2.

FIG. 13 is an enlarged partial cross-sectional view depicting the pressurized leak-proof sealing engagement between the cap 119 and upper barrel portion 120 from FIG. 2 wherein the cap 119 has a built-in or integral recess groove 121 providing a sealing pocket with the top sealing surface 122 on the upper barrel portion 120.

To further enhance this leak-proof sealing engagement, the cap threads 123, once engaged, form a downward pressure seal ring 124 to provide a leak-proof pressure seal of up to 40 psi once the cap 119 is fully threadably engaged with the upper barrel portion 120. Additionally, grip projections 125 can be integrally molded into the cap 119 to aid in screwing the cap 119 onto the upper barrel portion 120, if desired.

Figure 14:
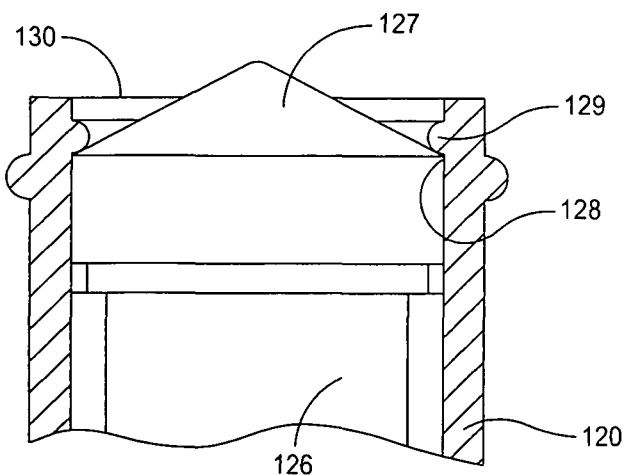
FIG. 14 is an enlarged partial cross-sectional view of the upper portion of the barrel and piston engagement wherein the barrel has a molded in annular ring preventing the piston from exiting the upper barrel.

FIG. 14 depicts how the upper barrel portion 120 may include an internally molded-in or integral annular ring 129 which acts as a stop against the piston top surface 128 on the piston grommet 127 thereby preventing the grommet 127 from being pushed out the top surface opening 130 on barrel 120 during any forward depression of the piston 126 within the barrel 120.

The design shown and described in FIG. 14 is an alternate configuration to prevent resilient, smooth-surfaced Kraton or silicone molded grommet 127 from advancing out of the barrel portion 120 from the previously shown and described means for preventing piston 126 advancement shown in FIGS. 11 and 12.

Figure 15:
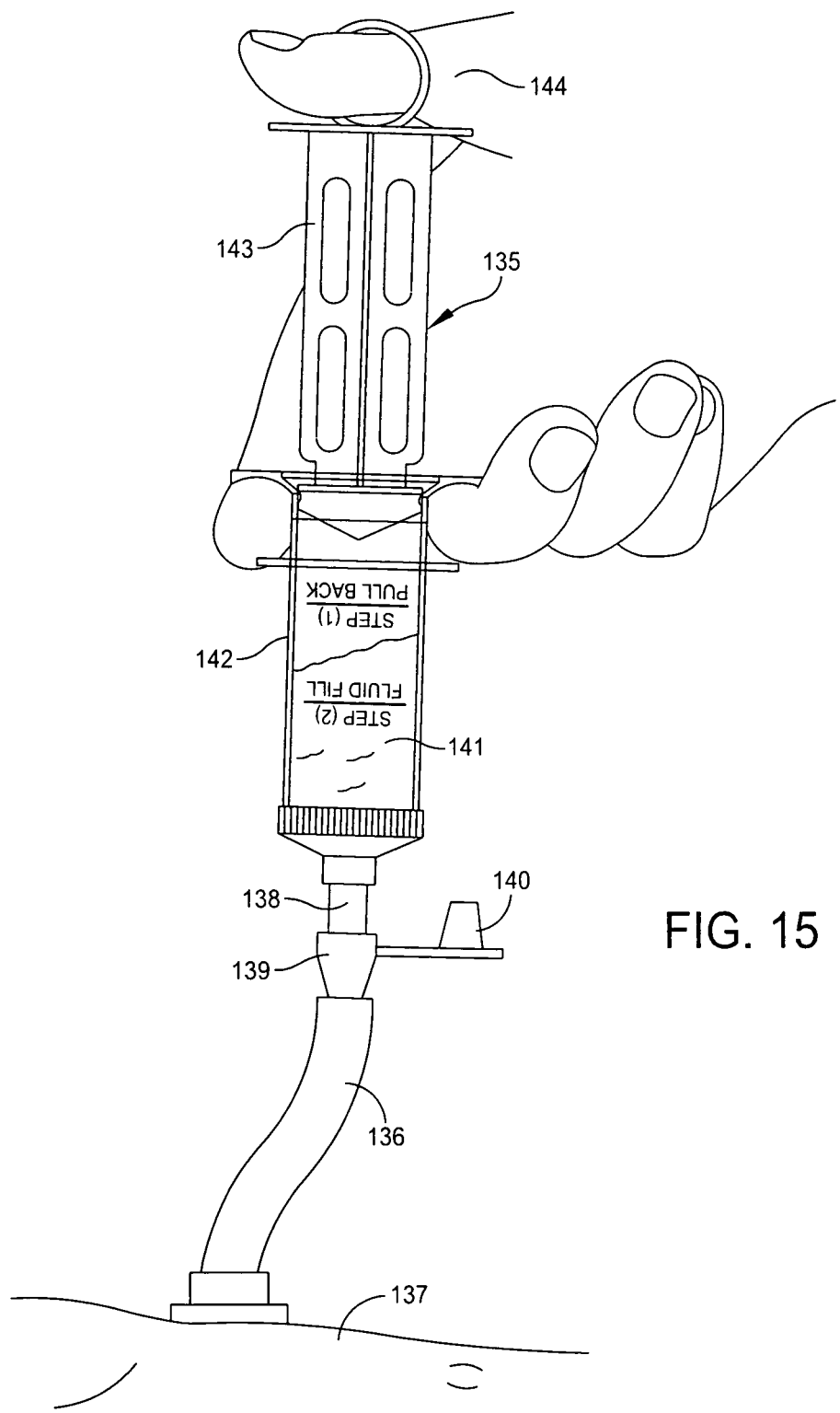
FIG. 15 is a front view of the syringe device administering crushed and dissolved medication into a patient's feeding tube.

FIG. 15 is a front view of the medication syringe infuser device 135 as shown in FIGS. 11 and 12 connected to a patient's gastrostomy feeding tube 136 indwelling in a patient's abdominal stomach portion 137.

While the infuser device 135 is shown connected to a gastrostomy tube 136, it is readily apparent that infuser device 135 can also be utilized and connected to any type of enteral feeding tube such as a naso-enteric or jejunostomy tube. The syringe infuser device 135 has a catheter tip 138 that can be inserted into any type of enteric tube connector 139 typically having some type of closure cap 140

Crushed and dissolved medication 141 within the syringe infuser barrel portion 142 is administered directly into the patient's gastrostomy tube 136 by hand depressive action on the piston portion 143 using single hand and thumb 144 operation as depicted in FIG. 15. Of course, two-handed operation is always an option by using the syringe infuser device as shown in FIG. 1.

Once the crushed and dissolved medication 141 is administered, then the syringe tip 138 can be disconnected from the tube connector 139, and the infuser syringe device 135 can be refilled with flushing irrigation fluid to be reconnected to the tube 136 for a final flush of the tube 136 if desired.

As can be seen from the drawings and above descriptions thereof, the device provides a unique, easy to use, disposable device that is self-contained and inexpensive.

The device is unique in that the device meets all the recommendations for flushing enteral feeding tubes and diluting enteral medications as outlined in "Medication Administration Through Enteral Feeding Tubes", *American Journal of Health-System Pharmacy*, 2008; 65(24):2347-2357, Nancy Toedter Williams, Pharm. D., BCPS, BCNSP as well as in "Drug Administration through a Feeding Tube", *The Oley Foundation*, Albany, N.Y., and "Enteral Nutrition Practice Recommendations" *Journal of Parenteral and Enteral Nutrition*, Vol. 33, No. 2, 122-167 (2009).

It should be noted that variations in configurations, sizes, materials, or methodology for removing and/or securing the cap to the barrel can easily be designed or configured with attributes known in the art without departing from the unique, novel aspects of the underlying invention.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

I claim:

1. A method for diluting enteral medication so as to form diluted medication and then infusing said diluted medication into a patient using a combination medication dilutor and fluid infuser syringe device including a syringe including a barrel in turn having a top opening portion and a retractable and advanceable piston positioned within said barrel, having a removable and replaceable top cap with a non I.V. luer compatible tip: the method comprising the following steps, Step 1: removing the cap from the top opening of the barrel of the syringe device and retracting the piston positioned within the barrel to form a medication diluting receptacle chamber with the barrel;

Step 2: preparing all required medication including a crushed pill and/or liquid, and diluting fluid externally of said syringe device in a container entirely separate from and forming no part of said device and then manually pouring said all required medication and diluting fluid from said container through the top opening of the barrel into said diluting receptacle chamber;

Step 3: replacing the cap back onto the top opening and closing or otherwise sealing off the tip and then manually shaking the syringe device to dilute the entire amount of required medication and fluid contained within the diluting receptacle chamber; and Step 4: opening the tip and then manually depressing the piston so as to infuse the diluted medication through the tip and into the patient.

2. A method for diluting enteral medication so as to form diluted medication and then infusing said diluted medication using a combination medication dilator and fluid infusion syringe device having:

a diluting syringe including a barrel in turn having a top opening portion, a removable and replaceable cap having a tip opening configured to prevent misconnection with an I.V. catheter in turn having a closure, said cap engageable with the top opening portion on said barrel to both open the top opening portion upon removal of the cap and sealing off the top opening portion upon engagement of the cap, a retractable and advanceable piston positioned within said barrel and said piston forming an inner receptacle chamber within said barrel upon retraction of the piston, said top opening portion of said barrel permitting manual pouring acceptance of all required medication and diluting fluid from said container into said inner receptacle chamber when said cap is removed from said top opening and said piston is retracted, said inner receptacle chamber further acting as a shakable medication and fluid diluting dissolving chamber when said cap is replaced and said tip opening is closed, and said piston further acting as a means to infuse the diluted medication and fluid out said tip when said tip is opened and said piston is advanced: the method comprising the following steps, Step 1: removing the cap from the top opening of the barrel portion of the syringe device and retracting the piston positioned within the barrel portion to form a diluting receptacle chamber with the barrel;

Step 2: preparing all required medication including a crushed pill and/or liquid, and diluting fluid externally of said syringe device in a container entirely separate from and forming no part of said device and then manually pouring said all required medication and diluting fluid from said container through the top opening of the barrel into said diluting receptacle chamber;

Step 3: replacing the cap back onto the top opening and closing or otherwise sealing off the tip and then manually shaking the syringe device to dilute the entire amount of required medication and fluid contained within the diluting receptacle chamber; and Step 4: opening the tip and then manually depressing the piston so as to infuse said diluted medication through the tip and into the patient.

3. A method for diluting enteral pill medication so as to form diluted medication and then infusing said diluted medication into a patient using a combination medication dilutor and fluid infuser syringe device including a syringe including a barrel in turn having a top opening portion and a retractable and advanceable piston positioned within said barrel, having a removable and replaceable top cap with a non I.V. luer compatible tip: the method comprising the following steps, Step 1: removing the cap from the top opening of the barrel of the syringe device and retracting the piston positioned within the barrel to form a medication diluting receptacle chamber with the barrel;

Step 2: crushing said pill medication externally of said syringe device in a container entirely separate from and forming no part of said device and then manually pouring said crushed pill medication and diluting fluid from a second container through the top opening of the barrel into the diluting receptacle chamber;

Step 3: replacing the cap back onto the top opening and closing or otherwise sealing off the tip and then manually shaking the syringe device to dilute said crushed pill medication and fluid contained within the diluting receptacle chamber; and Step 4: opening the tip and then manually depressing the piston so as to infuse the diluted medication through the tip and into the patient.

4. The method of claim 3 wherein the medication is in the form of a tablet or a liquid or a powder.

* * * * *